United States Patent
Hejazi et al.

(10) Patent No.: US 9,612,222 B2
(45) Date of Patent: Apr. 4, 2017

(54) DETECTION OF TARGET DNA SEQUENCES USING DOUBLE-STRANDED OLIGONUCLEOTIDES

(76) Inventors: Mohammad Saeid Hejazi, Tabriz (IR); Esmaeel Alipour, Tabriz (IR); Elaheh Dalir Abdolahinia, Tabriz (IR); Sanam Arami, Tabriz (IR)

( * ) Notice: Subject to any disclaimer, the term of this patent is extended or adjusted under 35 U.S.C. 154(b) by 0 days.

(21) Appl. No.: 12/696,508

(22) Filed: Jan. 29, 2010

(65) Prior Publication Data

US 2011/0186448 A1    Aug. 4, 2011

(51) Int. Cl.
G01N 27/26 (2006.01)
G01N 27/327 (2006.01)

(52) U.S. Cl.
CPC ..... *G01N 27/3277* (2013.01); *G01N 27/3275* (2013.01); *G01N 27/3276* (2013.01)

(58) Field of Classification Search
CPC ............ G01N 27/3275; G01N 27/3276
USPC ............ 205/775, 792; 204/403.01; 435/6
See application file for complete search history.

(56) References Cited

U.S. PATENT DOCUMENTS

2002/0177135 A1* 11/2002 Doung et al. .............. 435/6

OTHER PUBLICATIONS

Wang, Biosens. & Bioelect. 13 (1998) 757-762.*
Hashimoto et al. Lab on a Chip, 2001, 1, 61-63.*
Kara et al. Electrochemistry Communications 4 (2002) 705-709.*
Ozkan et al. Electrochemistry Communications 4 (2002) 796-802.*
Ozkan et al. Bioelectrochemistry 58 (2002) 119-126.*
Palecek et al. Biosensors & Bioelectronics 13 (1998) 621-628.*
Nielsen, Curr Med Chem. Apr. 2001;8(5):545-50.*
Ozkan et al. Electrochem. Comm. 4 (2002) 796-802.*
Baker et al. J. Am. Chem. Soc., 2006, 128, 8484-8492.*

* cited by examiner

*Primary Examiner* — Luan Van
*Assistant Examiner* — Steven Rosenwald (57) ABSTRACT

A method of detection and discrimination of target DNA sequences and of single nucleotide polymorphisms (SNPs) directly on double-stranded DNA (dsDNA) samples without the need for denaturation of the target dsDNAs. This is achieved by the use of a PNA chain as a probe. This probe is self-assembled on a gold electrode; hybridization of the probe with the target dsDNA forms a PNA-dsDNA hybrid. The hybrid is then labeled with a mediator, and the PNA-dsDNA hybridization is monitored. Monitoring of the hybrid formation can be achieved using an electrochemical approach. This method is able to detect and discriminate target DNA sequences and SNPs on ds-oligonucleotides. Furthermore, this method is able to detect and discriminate target DNA sequences and SNPs on double-stranded PCR products.

11 Claims, 4 Drawing Sheets

DETECTION OF TARGET DNA SEQUENCES USING DOUBLE-STRANDED OLIGONUCLEOTIDES

SPONSORSHIP STATEMENT

This application has been financially sponsored for international filing by the Iranian Nanotechnology Initiative Council, which does not have any rights in this application.

FIELD OF THE INVENTION

The present invention relates to a method of detection and discrimination of target DNA sequences and single nucleotide polymorphisms (SNPs). More specifically, the present invention relates to a method of detection and discrimination of target DNA sequences and SNPs directly on double-stranded oligonucleotides or PCR products without denaturing the target double-stranded oligonucleotides (ds oligonucleotides) or PCR products, using PNA probes and based on PNA-dsDNA hybrid formation.

DESCRIPTION OF RELATED ART

The detection of specific target DNA sequences is of increasing importance in disease diagnostics, forensics, biotechnology, and many other applications. DNA detection methods most commonly used include the use of probe DNA, blot methods (such as the Southern blot), and polymerase chain reaction (PCR).

Probe DNA can be used to detect a specific nucleic acid fragment. In this method, a nucleic acid fragment is detected by a hybridization reaction between the fragment and a probe DNA with a complementary (according to the rules of Watson-Crick base pairing) sequence. A solid carrier is commonly used on which to affix the probe DNA; this carrier/probe DNA combination is known as a DNA chip. The carrier can be made of a variety of substances, including glass, plastic, or an electroconductive material (for example, see U.S. Pat. No. 6,713,255). Basically, detection of DNA using a probe involves labeling a DNA fragment with a detectable molecule (such as a fluorescent or radioisotope label, or biotin), or the labeling of probe DNA with an electrochemical label. Probe DNA that is complementary to the sequence of the sample nucleic acid will bind to the sample, which is then detectable using an applicable method (fluorometry, autoradiography, the biotin-avidin method, voltammetry, etc.).

DNA blotting techniques involve the fractionalization of a sample of DNA by gel electrophoresis. Once the DNA is on the gel, it is denatured to create single-stranded DNA (ssDNA). The ssDNA is transferred from the gel to a nitrocellulose membrane and fixed onto the membrane by heating it in a vacuum, and is then incubated with a labeled ssDNA probe that is complementary to a specific DNA sequence, and is thus capable of hybridizing to any fragments in the sample having that sequence. Any unbound probe is washed away, and bound probes are visualized using an appropriate detection method (for example, see G. Karp, Cell and Molecular Biology: Concepts and Experiments, 757, Fifth Ed., John Wiley & Sons, Inc. (2008)).

PCR can also be used to detect target DNA. This method involves the use of PCR oligonucleotide primers that are complementary to a target nucleic acid sequence within a sample. These primers and other required PCR ingredients are added to a mixture, and PCR is allowed to take place. A PCR product will only be produced if the target DNA is present in the sample (for example, see G. Karp, Cell and Molecular Biology: Concepts and Experiments, 765, Fifth Ed., John Wiley & Sons, Inc. (2008)).

The detection of single nucleotide polymorphisms (SNPs) is also of increasing scientific, medical, and pharmaceutical importance. SNPs are discrepancies in the DNA sequence between two individuals of the same species. SNPs are not only implicated in disease development, but also may be part of the reason why individuals react differently to the same pharmaceutical drugs (for example, see SNPs: Variations on a Theme, http://www.ncbi.nih.gov/About/primer/snps.html). Hybridization methods (such as dynamic allele-specific hybridization (DASH), use of molecular beacons, and SNP microarrays) are commonly used to find these small changes. Enzyme based methods (such as restriction fragment length polymorphism (RFLP), use of Flap endonuclease ("invader assay"), use of 5'-nuclease ("Taqman assay"), and oligonucleotide ligase assay) are also used (for example, see R. Rapley & S. Harbron, Molecular Analysis and Genome Discovery, 42-59, John Wiley & Sons, Ltd. (2004)).

In addition to using DNA nucleic acid as a probe for the detection of target DNA sequences and SNPs, peptide nucleic acid (PNA) is also usable in certain applications. PNA is a synthetic analogue of DNA in which the DNA-type phosphate sugar backbone is replaced by a peptide backbone. Like biological nucleic acids, PNA can hybridize to DNA and RNA with sequence specificity; however, because PNA is not a naturally occurring compound, it is not susceptible to enzymatic degradation and has a longer shelf life (for example, see U.S. Pat. No. 6,280,946). Additionally, PNA's lack of a charge causes PNA/DNA to hybridize more readily and with greater strength than DNA/DNA (for example, see E. Ortiz et al., Cellular Probes, vol. 12, pp. 219-226 (1998)). This higher affinity allows significantly shorter PNA oligomers to be used in probe-based analyses as opposed to the 25- to 30-unit length typical for an oligonucleotide probe required to obtain a stable hybrid (for example, see U.S. Pat. No. 5,985,563).

PNAs have a higher thermal instability of mismatching bases than DNA/DNA combinations because PNAs exhibit a greater specificity for their complementary nucleic acids than do traditionally used nucleic acid probes of corresponding sequence (for example, see U.S. Pat. No. 5,985,563).

PNA has been used in several nucleic acid detection techniques, such as: (1) use in a PNA chip used for highly sensitive qualitative analysis of a nucleic acid fragment complementary to the chip's PNA fragment (U.S. Pat. No. 6,713,255); (2) PNA probes for the universal detection of bacteria and/or eucarya (U.S. Pat. No. 6,280,946); (3) PNA probes for the detection of ribosomal RNA (U.S. Pat. No. 5,985,563); and (4) use in molecular beacons for rapid detection of PCR amplicons (E. Ortiz et al. (1998)). PNA is also used, for example, in (5) enhancing amplification in PCR (U.S. Pat. No. 5,656,461); and (6) inclusion in a PNA-DNA-PNA chimeric macromolecule that has increased nuclease resistance, increased binding affinity to a complementary nucleic acid strand, and that activates RNase H enzyme (U.S. Pat. No. 5,700,922).

As one of ordinary skill in this art understands, however, is that all of these DNA- and SNP-detection techniques and PNA applications have in common the requirement that, at some point in the process, target double-stranded DNA (dsDNA) be denatured into ssDNA. In fact, nucleic acid hybridization is based on the phenomenon that complementary strands of nucleic acids from different sources can anneal to each other and create a hybrid double-stranded molecule. Nucleic acid hybridization is the driving force behind the use of DNA probes, blotting techniques, and PCR.

The prior art, although teaching the highly stable and specific binding of PNA to DNA, also requires the denaturation of dsDNA into ssDNA. In other words, PNA binds to ssDNA to create a double-stranded detectable hybrid. Denaturation of DNA represents a time-consuming step in nucleic acid detection, and can also provide the opportunity for machine or human error in a procedure.

SUMMARY OF THE INVENTION

It is thus the purpose of the present invention to provide a more streamlined, simplified method for the detection of target DNA sequences and SNPs that may greatly reduce the assay time and the number of required procedures in the detection protocol.

The present invention achieves these goals by providing a method for the detection and discrimination of target DNA sequences and SNPs directly on a double-stranded oligonucleotide (ds-oligonucleotide) chain or PCR product through the use of PNA-dsDNA hybrid formation.

Generally, this invention relates to a method of using the PNA-dsDNA hybrid to find a target DNA sequence within a sample of DNA. The invention also relates to a method of using the PNA-dsDNA hybrid to discriminate between DNA sequences within a sample that are complementary to the PNA probe, and sequences that are either non-complementary or contain SNPs.

In one embodiment, this invention relates to a PNA-based electroactive-label-mediated electrochemical method for the detection and discrimination of target DNA sequences directly on ds-oligonucleotides. This method uses a PNA probe that is complementary to a target DNA sequence and thus forms a PNA-dsDNA hybrid with the ds-oligonucleotide.

In another embodiment, this invention relates to a PNA-based electroactive-label-mediated electrochemical method for the detection and discrimination of single nucleotide polymorphisms (SNPs) within DNA sequences directly on ds-oligonucleotides. This method uses a PNA probe that is complementary to a target DNA sequence and thus forms a PNA-dsDNA hybrid with the ds-oligonucleotide.

In another embodiment, this invention relates to a PNA-based electroactive-label-mediated electrochemical method for the detection and discrimination of target DNA sequences directly on double-stranded PCR products. This method uses a PNA probe that is complementary to a target DNA sequence and thus forms a PNA-dsDNA hybrid with the double-stranded PCR product.

In another embodiment, this invention relates to a PNA-based electroactive-label-mediated electrochemical method for the detection and discrimination of single nucleotide polymorphisms (SNPs) within DNA sequences directly on double-stranded PCR products. This method uses a PNA probe that is complementary to a target DNA sequence and thus forms a PNA-dsDNA hybrid with the double-stranded PCR product.

BRIEF DESCRIPTION OF THE DRAWINGS

The present invention is illustrated by way of example and not by limitation in the accompanying drawings, in which.

DETAILED DESCRIPTION THE INVENTION

Definitions

"PNA" or "peptide nucleic acid" is used herein to mean any oligomer, linked polymer or chimeric oligomer, comprising two or more PNA subunits (residues), with a peptide backbone comprised of repeating N-(2-aminoethyl)-glycine units linked by peptide bonds. This definition also includes any of the compounds referred to or claimed as peptide nucleic acids in U.S. Pat. Nos. 5,539,082; 5,527, 675; 5,623,049; 5,714,331; 5,736,336; 5,773,571; or 5,786,461 (all of which are herein incorporated by reference). The term "peptide nucleic acid" or "PNA" shall also apply to polymers comprising two or more subunits of those nucleic acid mimics described in the following publications: Diderichsen et al., *Tett. Lett.* 37: 475-478 (1996); Fujii et al., *Bioorg. Med. Chem. Lett.* 7: 637-627 (1997); Jordan et al., *Bioorg. Med. Chem. Lett.* 7: 687-690 (1997); Krotz et al., *Tett. Lett.* 36: 6941-6944 (1995); Lagriffoul et al., *Bioorg. Med. Chem. Lett.* 4: 1081-1082 (1994); Lowe et al., *J. Chem. Soc. Perkin Trans.* 1: 539-546 (1997); Lowe et al., *J. Chem. Soc. Perkin Trans.* 1: 555-560 (1997); Petersen et al., *Bioorg. Med. Chem. Lett.* 6: 793-796 (1996); Deiderichsen, U., *Bioorganic & Med. Chem. Lett.* 8: 165-168 (1998); Cantin et al., *Tett. Lett.* 38: 4211-4214 (1997); Ciapetti et al., *Tetrahedron* 53: 1167-1176 (1997); Lagriffoule et al., *Chem. Eur. J.* 3: 912-919 (1997); and WIPO patent application WO96/04000 (Shah et al., "Peptide-based nucleic acid mimics (PENAMs)").

"PNA probe" is used herein to mean a PNA sequence that is complementary to at least a portion of a target DNA sequence. The PNA probe may also include a thiolated head group and a linker segment, but does not include any tag, label, or marker used for detection of the probe using radioactive detection, fluorescence, or any other detection methods.

"Target DNA" or "target sequence" is used herein to mean the nucleic acid sequence of sample DNA to be detected in an assay and to which at least a portion of the probing PNA sequence is designed to hybridize.

"PNA-dsDNA" or "PVA-dsDNA hybrid" is used herein to mean the pairing of PNA and double-stranded DNA, which results in a multiple-stranded hybrid.

"Double-stranded oligonucleotide" or "ds-oligonucleotide" is used herein to mean a short synthetic polymer comprised of two complementary strands of at least two nucleotides.

"Self-assembled monolayer" or "SAM" is used herein to mean a self-organized layer of amphiphilic molecules, such molecules comprising a head group with a particular affinity for the surface of a specific substrate, and a tail containing any of a variety of functional groups.

"Single base mutation" or "SBM" is used herein to mean a DNA sequence variation in which a single base pair is substituted (changed), added (inserted), or deleted (removed), and which is either naturally occurring or artificially induced.

"Single nucleotide polymorphism" or "SNP" is used herein to mean a discrepancy in the DNA sequence in at least one base pair between two individuals of the same species. The terms of SNP and SBM have the same meaning in this art.

Description of the Invention

The present invention allows for the detection and selective discrimination of target DNA sequences directly on ds-oligonucleotides and double-stranded PCR products. Furthermore, the detection of DNA single base mutations on ds-oligonucleotides and double-stranded PCR products is also taught. Detection procedure is carried out without the need for denaturation of a dsDNA sample into ssDNA. This strategy is a label- and enzyme-free method that relies on direct interaction of a PNA probe with the target dsDNA. Accordingly, it is a simplified and rapid DNA and mutation detection protocol. The method could be considered as a fundamental platform for the development of further DNA detection techniques based on PNA-dsDNA hybridization.

It has been discovered that PNA can form not only a PNA-ssDNA duplex, as seen in traditional hybridization methods, but can also form other structures including a PNA-dsDNA hybrid (for example, a PNA-dsDNA triplex hybrid) when pyrimidine or purine bases of the PNA fit into the major groove of the DNA double helix. Generally, two homopyrimidine PNA molecules displace the duplex DNA pyrimidine strand and form a hybrid with the purine DNA strand (such structure commonly called a "P-loop") (for example, see M. D. Frank-Kamenetskii et al., Annu. Rev. Biochem., vol. 64, pp. 64-95 (1995)). It is no longer required that the ds-oligonucleotide and PCR product be denatured into a ssDNA in order to detect a target DNA sequence and this hybrid is used as a method to detect target DNA sequences directly on the ds-oligonucleotides and double-stranded PCR products without denaturing the target dsDNA into ssDNA.

Additionally, sequence mutations may also be detected without denaturing the target DNA. This is based on the observation that, although PNA has a high binding affinity for complementary DNA, it binds less tenuously to a mismatched DNA sequence than two non-complementary DNA sequences would bind to each other. Therefore, a low occurrence of binding between a PNA probe and a target DNA sequence indicates that a SNP exists in the sample DNA sequence, as opposed to the high occurrence of binding that is expected between a PNA probe and complementary DNA sequence. Furthermore, because of the ability to use a short fragment of PNA as an effective probe, mutations can be isolated more specifically in a given DNA sequence.

The PNA probe method of this invention is particularly useful for the detection and discrimination of target DNA sequences and SNPs directly on ds-oligonucleotides and PCR products from clinical specimens. There is an increased recognition of the importance of SNPs in disease development, and the method disclosed herein provides an effective way of detecting these mutations.

This invention broadly comprises a PNA-based electroactive label-mediated electrochemical method for the detection and discrimination of a target DNA sequence and SNP directly on dsDNA using a PNA probe, using the PNA-dsDNA hybrid formation that occurs between the dsDNA and PNA probe.

More specifically, the above-described method comprises the use of a PNA probe that has not been coupled with any marker or label, and that contains only a functional group (here, a thiol group provided by cysteine) that is connected to the probe with a linker segment (here, 8-amino-3,6-dioxa-octanoic acid).

The above-described method also comprises the use of a gold electrode (AuE), onto which the thiolated PNA probe attaches (via the thiol group), resulting in the formation of a self-assembled monolayer (SAM).

The AuE/SAM is then exposed to a sample of DNA. If the sample contains the target DNA sequence, results in the formation of a stable PNA-dsDNA hybrid resulting from the interaction of the PNA probe with the dsDNA, one strand of which is completely complementary to the probe.

Monitoring of the hybrid formation can be achieved using an electrochemical approach. In a preferred embodiment, the formation of the PNA-dsDNA hybrid is monitored electrochemically following interaction of the hybrid with an electroactive label such as Methylene blue (MB). Neither the PNA nor target DNA sequences are tagged, labeled, or marked with any tag, label, enzyme or marker prior to this step; it is only after mixing the PNA probe and dsDNA sample that MB is added. The preferred electrochemical method for monitoring hybrid formation is differential pulse voltammetry (DPV).

Preferred Embodiments

In one embodiment, this invention relates to a PNA-based electroactive-label-mediated electrochemical method for the detection and discrimination of target DNA sequences directly on ds-oligonucleotides. This method uses a PNA probe that is complementary to a target DNA sequence and thus forms a PNA-dsDNA hybrid with the ds-oligonucleotide.

In another embodiment, this invention relates to a PNA-based electroactive-label-mediated electrochemical method for the detection and discrimination of single nucleotide polymorphisms (SNPs) within DNA sequences directly on ds-oligonucleotides. This method uses a PNA probe that is complementary to a target DNA sequence and thus forms a PNA-dsDNA hybrid with the ds-oligonucleotide.

In another embodiment, this invention relates to a PNA-based electroactive-label-mediated electrochemical method for the detection and discrimination of target DNA sequences directly on double-stranded PCR products. This method uses a PNA probe that is complementary to a target DNA sequence and thus forms a PNA-dsDNA hybrid with the double-stranded PCR product.

In another embodiment, this invention relates to a PNA-based electroactive-label-mediated electrochemical method for the detection and discrimination of single nucleotide polymorphisms (SNPs) within DNA sequences directly on double-stranded PCR products. This method uses a PNA probe that is complementary to a target DNA sequence and thus forms a PNA-dsDNA hybrid with the double-stranded PCR product.

All electrochemical experiments were performed in a 5 ml volume cell, connected to an AUTOLAB PGSTAT 30 electrochemical analysis system and GPES 4.9 software package (Eco Chemie., the Netherlands). This three-electrode system was composed of a gold disk electrode (having a diameter of 3 mm, Bioanalytical Systems (BAS), West Lafayette, Ind.), a saturated calomel electrode (SCE) as the reference electrode, and a platinum wire as the auxiliary electrode. Supporting electrolyte was deoxygenated by purging with nitrogen gas for 10 minutes prior to measurements, and the cell was blanketed with nitrogen for the duration of the experiments. All of the electrochemical experiments were carried out at laboratory ambient temperature.

Preparation of the Working Electrode

A gold disk electrode (having a diameter of 3 mm, Bioanalytical Systems (BAS), West Lafayette, Ind.) was used for all the experiments. The electrode was polished with wet alumina slurry (Alpha and Gamma Micropolish II deagglomerated alumina, Buehler, Lake Bluff, Ill.) on a felt pad for at least 10 minutes and rinsed repeatedly with water. The polished electrode was then dipped in a solution of 1:1 EtOH—$H_2O$ containing 0.5 M $NaBH_4$ for about 20 minutes. The electrode was then treated in 0.05 M $H_2SO_4$ with a cycling of the potential between −0.3 and 1.5 V with a scan rate of 0.1 Vs-1 until the cyclic voltammogram did not change (indicating that the electrode surface was clean). Finally, the electrode was rinsed with water before probe self-assembly.

PNA self-assembly onto the surface was performed as follows: The electrode was placed upside down in a disposable glass tube. An aliquot of 5 μL of the 50 μM PNA probe was deposited onto the gold electrode. The tube was sealed to prevent water evaporation and left for self-assembly at room temperature overnight. The electrode was then rinsed with water and dipped in an aqueous 1 mM 6-mercapto-1-hexanol (MCH) solution at room temperature for 30 minutes. MCH deposition is important both to competitively remove non-covalently adsorbed PNA molecules and to fill "pinholes" within the PNA monolayer. The electrode was washed repeatedly with water before every use.

Evaluation of PNA Self-Assembled Monolayer Formation

The extent of probe self-assembly was monitored by the probe influence on the electrochemical signal of $Fe(CN)_6^{3-}$/$Fe(CN)_6^{4-}$ system on the pretreated AuE based on the decline in the height of the $Fe(CN)_6^{3-}$/$Fe(CN)_6^{4-}$ redox peaks. For this purpose, the electrode was scanned between −0.5 and 0.6 V in 10 mM $K_3Fe(CN)_6$+10 mM $K_4Fe(CN)_6$ solution.

PNA-dsDNA Hybridization

Hybridization between the probe and PCR products was carried out following gel extraction of the desired DNA bands from agarose gel using QIAquick Purification Kit (QIAGEN, Germany). The extracted DNA fragments were used for the hybridization without denaturation (i.e. as a double-stranded structure).

Hybridization between the PNA probe and ds-oligonucleotides or double-stranded PCR products was performed using the direct dropletting method, the same protocol used for the probe self-assembly on the electrode. A 5 μL droplet of ds-DNA sample was deposited onto the gold electrode. The tube was sealed to prevent water evaporation and kept at room temperature during overnight hybridization, resulting in the formation of the PNA-dsDNA hybrid. The PNA-dsDNA/AuE was rinsed with water.

The target DNA molecules were all used in their stock concentration (100 μM) as a 5 μL drop.

Label Binding to the Hybrid

Methylene blue was accumulated on the PNA self-assembled AuE by immersing the modified electrode into the 20 mM Tris-HCl buffer (pH 7.0) containing 20 μM MB and 20 mM NaCl for 5 minutes with 200 rpm stirring without applying any potential to this electrode. Once MB was accumulated, the electrode was rinsed with 20 mM Tris-HCl buffer (pH 7.0) for 20 seconds. The same protocol was applied for the accumulation of MB on the bare electrode and probe-modified electrodes following the hybridization with dsDNA molecules.

Voltammetric Measurements

The oxidation signal of the accumulated MB was measured by using differential pulse voltammetry (DPV) in 20 mM Tris-HCl buffer (pH 7.0) containing 20 mM NaCl and scanning the electrode potential between 0.20 and −0.60 V at a pulse amplitude of 25mV. The raw data were treated using the Savitzky and Golay filter (level 2) of the GPES software, followed by the GPES software moving average baseline correction using a "peak width" of 0.01

Preliminary Investigation

Once the SAM formation of the PNA probe on the AuE was confirmed using the $Fe(CN)_6^{3-}$/$Fe(CN)_6^{4-}$ redox system, SAM formation and time and probe concentration variables, which affect the performance of the sensor, were studied and special emphasis was given to the optimization of these experimental variables.

Figure 1:
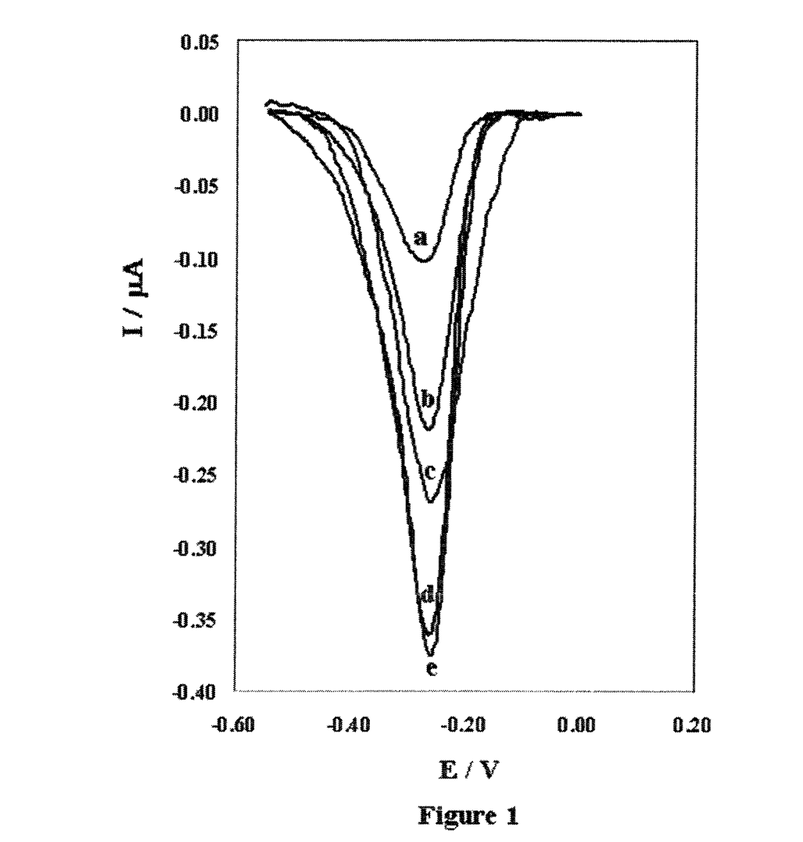
FIG. 1 shows the differential pulse voltammograms for the oxidation signal of MB following self-assembly of 100 µM of the PNA probe on the gold electrode (AuE) for different time durations including: 30 minutes (curve a), 1 hour (curve b), 7 hours (curve c), overnight (curve d), and 3 days (curve e)

In order to obtain the optimum self-assembly time, self-assembly of the PNA on the AuE was conducted for different time durations. FIG. 1 shows the differential pulse voltammograms for the oxidation signal of MB following self-assembly of 100 μM of the PNA probe on the AuE for different times including: 30 minutes (curve a), 1 hour (curve b), 7 hours (curve c), overnight (curve d), and 3 days (curve e). As seen in FIG. 1, the MB oxidation signal elevated as the self-assembly time increased to about overnight and maintained constant for 3 days. Therefore, overnight incubation was suggested as optimum time for self-assembly of PNA on the AuE.

The effect of PNA concentration on the self-assembly of the PNA on the electrode was studied using DPV measurements of MB signals following self-assembly of the PNA on the AuE using PNA solutions of 10 μM, 25 μM, 50 μM, and 100 μM. The results obtained from the Voltammetric measurements revealed that the MB oxidation signal elevated as the PNA concentration increased (104.8±16.7 nA (shown as an oxidation current of −0.1048±0.0167I/μA), 181.5±9.9 nA (shown as an oxidation current of −0.1815±0.0099 I/μA), 258.2±14.9 nA (shown as an oxidation current of −0.2582±0.0149 I/μA), and 359.1±22.4 nA (shown as an oxidation current of −0.3591±0.0224 I/μA) for 10, 25, 50, and 100 μM PNA concentration, respectively). Therefore, 50 μM was determined to be a proper and moderate PNA concentration for self-assembly of the probe on the AuE.

The following examples demonstrate in greater detail the procedures that can be used in the present invention. The DNA and PNA sequences used herein are, however, only suggestive, and are not intended to limit the scope of the invention in any way. One skilled in the art understands how to substitute and/or adapt the PNA sequence to investigate any desired target DNA sequence or SNP.

Example 1

Preparations

Preparation of PNA Probe

PNA probe P275 was obtained from PANAGENE and DNA oligonucleotides were supplied by Eurofins MWG Operon.

A 13-mer PNA oligonucleotide (P275) corresponding to the sense strand of human uridin diphosphate glucuronosyl-transferase 1A9 (UGT1A9) (SEQ ID NO: 8) gene promoter region was used as the probe. P275 had a sequence of Cys-OO- AGT TTA GTA GCA G, where "cys" was cysteine amino acid and "O" was an 8-amino-3,6-dioxa-octanoic acid linker. The 13-nucleic acid chain of P275 is identified as SEQ ID NO:1.

The cysteine at the N-terminal of the probe provided a thiol group that allowed covalent binding of the probe to the electrode surface, and the "O" linker separated the hybridization segment from the thiolated terminal. P275 (SEQ ID NO: 1) covered 13nucleotides of the promoter region of the UGT1A9 (SEQ ID NO: 8) gene, from nucleotides −280 to −267 from the start codon including (A/T) SNP at position −275.

Two DNA oligonucleotides were used for preparation of the complementary UGT ds-oligonucleotide: DC275 (5'-CTG CTA CTA AAC T-3') (SEQ ID NO: 2), which was complementary to the probe; and D275 (5'-AGT TTA GTA GCA G-3') (SEQ ID NO: 3), which was identical to the probe.

The following DNA oligonucleotides, which corresponded to the human interleukin-2gene, were used for preparation of the non-complementary IL-2 ds-oligonucleotide hIL-2(5'-GGA GGA AGT CGT AAA TTT AG-3') (SEQ ID NO: 4) and chIL-2 (5'-CTA AAT TTA CGA CTT CCT CC-3') (SEQ ID NO: 5).

The following DNA oligonucleotides were used for preparation of the UGT.SBM ds-oligonucleotide containing a single base mismatch with the PNA probe: DMM275 (5'-AGT TTA GAA GCA G-3') (SEQ ID NO: 6), which was identical to the probe with a single base substitution (T/A) at nucleotide 8; and DCMM275 (5'-CTG CTT CTA AAC T-3') (SEQ ID NO: 7), which was complementary to the probe with a single nucleotide mismatch (A/T) at the corresponding position; nucleotide 6 in this oligonucleotide.

Probe stock solution (100 µM) was prepared with 1% (v/v %) trifluoroacetic acid (TFA) solution. More diluted PNA solutions were prepared with 0.5 M acetate buffer solution (pH 4.8). Stock solutions of the DNA oligonucleotides (100 µM) were prepared in distilled, deionized, and sterilized water. More diluted solutions of the oligonucleotides were prepared using 0.01 M Tris-Cl buffer solution (pH 7.0).

Other chemicals were of analytical reagent grade. Distilled, deionized, and sterilized water was used in all solution preparation. All DNA solutions were kept frozen at −20° C. and all the experiments were performed at room temperature in an electrochemical cell.

Preparation of Double-Stranded Oligonucleotides

To prepare ds-oligonucleotides, equal concentrations (50 µM) of pair oligonucleotides were effectively mixed in a microtube. The mixed solution was then heated at 95° C. in a water bath for 10 minutes, and was then allowed to cool down gradually to room temperature.

(1) Human Genomic DNA Extraction

Human genomic DNA was extracted from a peripheral blood sample using a high-yield DNA purification kit (DNP™ Kit, CinnaGen, Inc.). Two hundred (200) µL of the sample blood was centrifuged at 3000 rpm for 10 minutes, from which the serum was then separated. The precipitated cells were suspended in lysis solution and lysed by incubation at 37° C. for 20 minutes. Precipitation solution was then added and the tube was placed at 20° C. for another 20 minutes. The solution was centrifuged at 14000 rpm for 20 minutes at 4° C., and then the supernatant was poured off. The DNA pellet was washed with wash buffer and dried. Extracted DNA was finally dissolved in solvent buffer and kept frozen at −20° C.

(2) Plant Genomic DNA Extraction

Genomic DNA extraction from *Thymus pubescens* was carried out according to the CTAB protocol described in J. J. Doyle et al., "Isolation of Plant DNA from Fresh Tissue," Focus vol. 12, pp. 13-15 (1990). Accordingly, leaves were immersed in liquid nitrogen and then ground into fine powder using a mortal and pestle. The powdered leaves were lysed by addition of a lysis solution (Tris-HCl 10 mM (pH 8.0), EDTA 1 mM, 1.4 M NaCl, 2% CTAB and 1% PVP) and incubation at 65° C. for 20 minutes. Genomic DNA extraction was carried out with equal volume of chloroform-isoamylalcohol (24:1) and precipitated from the aqueous phase with 0.6 volume (v/v) isopropanol. The extracted DNA was further purified using ethanol 70%.

PCR Amplification of Complementary and Mutant DNA Fragments

PCR amplification of complementary UGT1A9 (SEQ ID NO: 8) DNA fragments was conducted in the presence of human genomic DNA. This human genomic DNA served as the template DNA, using UGTF (5'-CTC TGG ACA GAG AGT ATT TGG-3') (SEQ ID NO: 9) and UGTRt (5'-TGC AAT GTT AAG TTT AGT AGC AG-3') (SEQ ID NO: 10) as forward and reverse primers, respectively.

In order to amplify the mutant form of the UGT1A9 (UGT1A9.SBM) (SEQ ID NO: 11) DNA fragment, containing a single base mutation, UGTF (SEQ ID NO: 9) and UGTRa (5'-TGC AAT GTT AAG TTT AGA AGC AG-3') (SEQ ID NO: 12) oligonucleotides were used as forward and reverse primers, respectively. It is noted that UGTRt (SEQ ID NO: 10) and UGTRa (SEQ ID NO: 12) have the same sequence with a single nucleotide substitution (T/A) at position 18.

PCR reactions contained about 100 ng template DNA, 0.1 µM of each primer, 1 mM of deoxynucleoside triphosphates (dNTPs), 1.5 mM $MgCl_2$, and 1 µl Taq DNA polymerase in a total volume of 50 µL. The amplification program consisted of the following steps:

(1) DNA denaturation at 95° C. for 5 minutes;
(2) thirty-five (35) amplification cycles, each cycle consisting of:
  (a) DNA denaturation at 95° C. for 1 minute;
  (b) primer annealing at 56° C. for 45 seconds; and
  (c) extension at 72° C. for 12 seconds; and
(3) final extension at 72° C. for 10 minutes.

PCR amplification of mutant UGT1A9 (UGT1A9.SBM) (SEQ ID NO: 11) was carried out with the same program except that the annealing temperature was reduced to 54° C.

The PCR products were separated on agarose gel and DNA bands were extracted from the gel using QIAquick PCR Purification Kit (QIAGEN, Germany). The pair primers UGTF/UGTRa (SEQ ID NO: 9 / SEQ ID NO: 12) and UGTF/UGTRt (SEQ ID NO: 9/SEQ ID NO: 10) cover the UGT1A9 (SEQ ID NO: 11) promoter region from nucleotide −426 to −258 from the start codon.

PCR Amplification of Non-Complementary DNA Fragments

Internal transcribed sequence ribosomal DNA (ITS rDNA) of the extracted genomic DNA from the plant *Thymus pubescens* (EU374715) (SEQ ID NO: 13) was amplified. The PCR reaction mixture (50 μL total volume) contained dNTPs (0.2 mM of each), 1.5mM $MgCl_2$, approximately 50-100 ng genomic DNA, 0.75 U Taq DNA polymerase, 5% dimethylsulfoxide, and 0.2 μM of each of the following primers: forward primer ITS1(5'-TCC GTA GGT GAA CCT GCG G-3') (SEQ ID NO: 14) and reverse primer ITS4(5'-TCC TCC GCT TAT TGA TAT GC-3') (SEQ ID NO: 15).

PCR amplification was carried out using the hot-start method and comprising the following steps:
 (1) initial DNA denaturation at 95° C. for 5 minutes;
 (2) thirty-five (35) amplification cycles, each cycle consisting of:
   (a) DNA denaturation at 94° C. for 30 seconds;
   (b) primer annealing at 50° C. for 30 seconds; and
   (c) extension at 72° C. for 1 minute; and
 (3) final extension at 72° C. for 5 minutes.

To amplify the IL-4 (SEQ ID NO: 16) promoter region, the following two primers were designed: forward primer IL4-F (5'-AGC TTT GGG AGA CTG CAG GTA-3') (SEQ ID NO: 17) and reverse primer IL4-R (5'-TGC TAG CAG GAA GAA CAG AG-3') (SEQ ID NO: 18). These primers covered the promoter region of the IL-4 (SEQ ID NO: 16) gene from nucleotide −999 to +48 from the start codon.

To amplify the IL-10 (SEQ ID NO: 19) promoter region, the following two primers were designed: forward primer IL10-F (5'-CCA AGA CAA CAC TAC TAA GG-3') (SEQ ID NO: 20) and reverse primer IL10-R (5'-TGC AGC TGT TCT CAG ACT G-3') (SEQ ID NO: 21). These primers covered the promoter region of the IL-10 (SEQ ID NO: 19) gene from nucleotide −1148 to +91 from the start codon.

The PCR reaction mixture (50 μl total volume) for amplification of the IL-4(SEQ ID NO: 16) promoter contained dNTPs (0.2 mM of each), 1.5 mM $MgCl_2$, 50 ng template DNA, 0.75 U Taq DNA polymerase, and 0.5 ° μM each of the IL4-F (SEQ ID NO: 17) and IL4-R (SEQ ID NO: 18) primers. PCR amplification comprised the following steps:
 (1) initial DNA denaturation at 95° C. for 5 minutes;
 (2) thirty-five (35) amplification cycles, each cycle consisting of:
   (a) DNA denaturation at 95° C. for 1 minute;
   (b) primer annealing at 54° C. for 45 seconds; and
   (c) extension at 72° C. for 85 seconds; and
 (3) final extension at 72° C. for 10 minutes.

PCR amplification of the IL-10 (SEQ ID NO: 19) promoter region was performed in the same manner as the IL-4 (SEQ ID NO: 16) promoter region amplification.

Example 2

Evaluations of ds-Oligonucleotide Using PNA Probe

Preparations

This example builds from the preparations described in Example 1.

Figure 2:
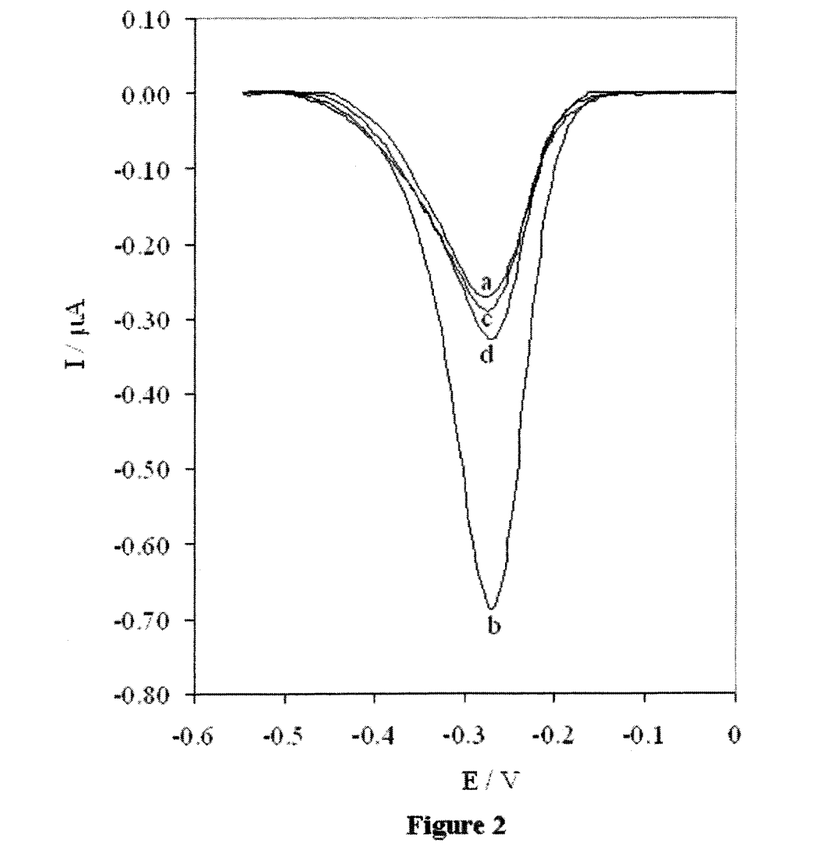
FIG. 2 shows the differential pulse voltammograms for the oxidation signal of MB following self-assembly of the 13-mer PNA probe on the AuE(curve a), after the hybridization with the complementary UGT ds-oligonucleotide (curve b), after the interaction with the non-complementary IL-2 ds-oligonucleotide (curve c), and after the interaction with the UGT.SBM ds-oligonucleotide containing one base mismatch (curve d)

The 13-mer PNA oligomer was self-assembled on the AuE as the probe and was hybridized with the complementary UGT ds-oligonucleotide. FIG. 2 shows the differential pulse voltammograms for the oxidation signal of MB following self-assembly of the probe on the AuE(curve a) and after the hybridization of the probe with the complementary dsDNA (curve b). The self-assembled probe displayed a current of 258.2±14.9 nA (shown as an oxidation current of −0.2582±0.0149 I/μA) following interaction with MB. However, a significant increase in the MB signal was observed following the hybridization of the PNA probe with the complementary ds-oligonucleotide (from 258.2±14.9 nA to 671.3±36.5nA) (shown as an oxidation current of −0.2582±0.0149 I/μA to −0.6713±0.0365 I/μA). The observed rise in MB signal is attributable to the intercalation of MB within the PNA-dsDNA structure as an intercalator. Therefore, the elevation in the MB signal is attributed to the hybridization of the PNA probe with the complementary ds-oligonucleotide on the electrode surface and consequently may be used for detection of a target DNA sequence.

Selectivity Study for ds-Oligonucleotide Detection

The hybridization of the PNA probe with the non-complementary dsDNA was carried out to assess selectivity of the proposed approach. For this purpose, IL-2 ds-oligonucleotide was prepared as a non-complementary ds-oligonucleotide and used for the selectivity study. Curve c in FIG. 2 shows the DPV for the oxidation signal of MB after interaction of the PNA modified electrode with the non-complementary ds-oligonucleotide. The interaction between the non-complementary ds-oligonucleotide and the probe-modified electrode did not lead to a significant increase in the MB signal (279.1±20.6 nA) (shown as an oxidation current of −0.2791±0.0206 I/μA), and the signal was nearly equal to that of the probe. This result indicates that only the complementary ds-oligonucleotide could form an entirely matched hybridized structure with the probe that results in the significant increase in the accumulation of MB.

A series of three repetitive measurements led to reproducible results and the relative standard deviation was 7.38% for the non-complementary sequence detection on ds-oligonucleotide. These results clearly demonstrate the feasibility of detection and discrimination of a target DNA sequence on a ds-oligonucleotide.

Single Base Mismatch Detection on ds-Oligonucleotide

The effective discrimination against a single base mismatch (SBM) directly on ds-oligonucleotide was investigated using UGT.SBM ds-oligonucleotide containing a single base mismatch (mutation). Curve d in FIG. 2 shows the DPV for the oxidation signal of MB after interaction of UGT. SNP ds-oligonucleotide with the PNA-modified electrode. As shown, in the presence of UGT.SBM ds-oligonucleotide, the MB signal was 320.8±27.5 nA (shown as an oxidation current of −0.3208±0.0275 I/μA). This current is significantly lower than the MB signal of the complementary ds-oligonucleotide due to the lack of entire hybridization between the probe and the single-base mismatched ds-oligonucleotide. The relative standard deviation was 8.57% for the detection of single base mismatch on the ds-oligonucleotide.

Example 3

Evaluations of PCR Product Using PNA Probe

Figure 3:
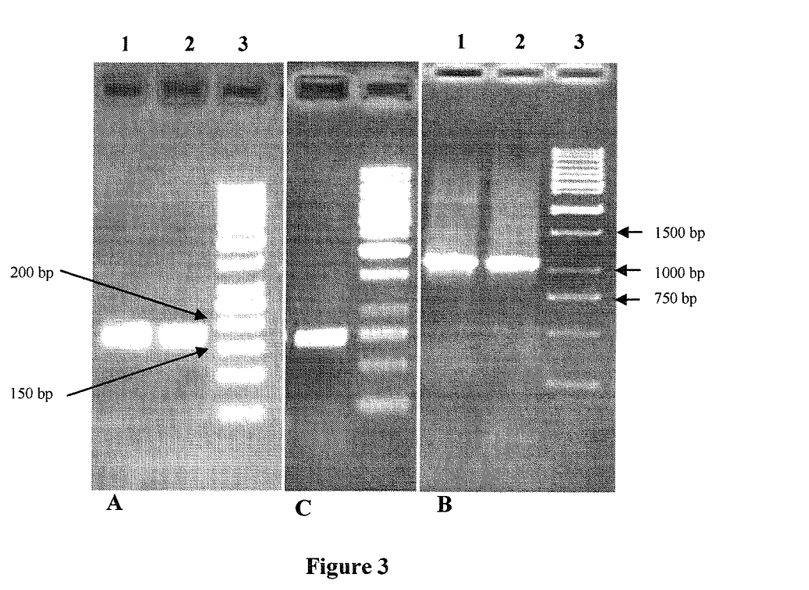
FIG. 3 shows the results of agarose gel electrophoresis of PCR products compared to 100 bp (A) and 1 kb (B and C) DNA ladders. PCR amplicons are of the following: complementary UGT1A9 with a length of 166 bp (A1) (SEQ ID NO: 8), the non-complementary internal transcribed sequence (ITS) with a length of 773 bp (B1) (SEQ ID NO: 13), IL-10 (C1) (SEQ ID NO: 19) and IL-4 (C2) (SEQ ID NO: 16) promoter regions with lengths of 1058 and 1047, respectively, and the mutant UGT1A9.SBM (SEQ ID NO: 11) containing one base mismatch with a length of 166 bp (A2)

Detection of Target DNA Sequence on Double-Stranded PCR Product without Denaturation PCR amplification of the complementary UGT1A9 (SEQ ID NO: 8) DNA fragment was conducted and followed by agarose gel electrophoresis. Electrophoresis of the complementary UGT1A9 (SEQ ID NO: 8) PCR sample showed a DNA band with a length of 166 bp, indicating the presence of the complementary UGT1A9 (SEQ ID NO: 8) DNA amplicon in the PCR sample (FIG. 3A).

Figure 4:
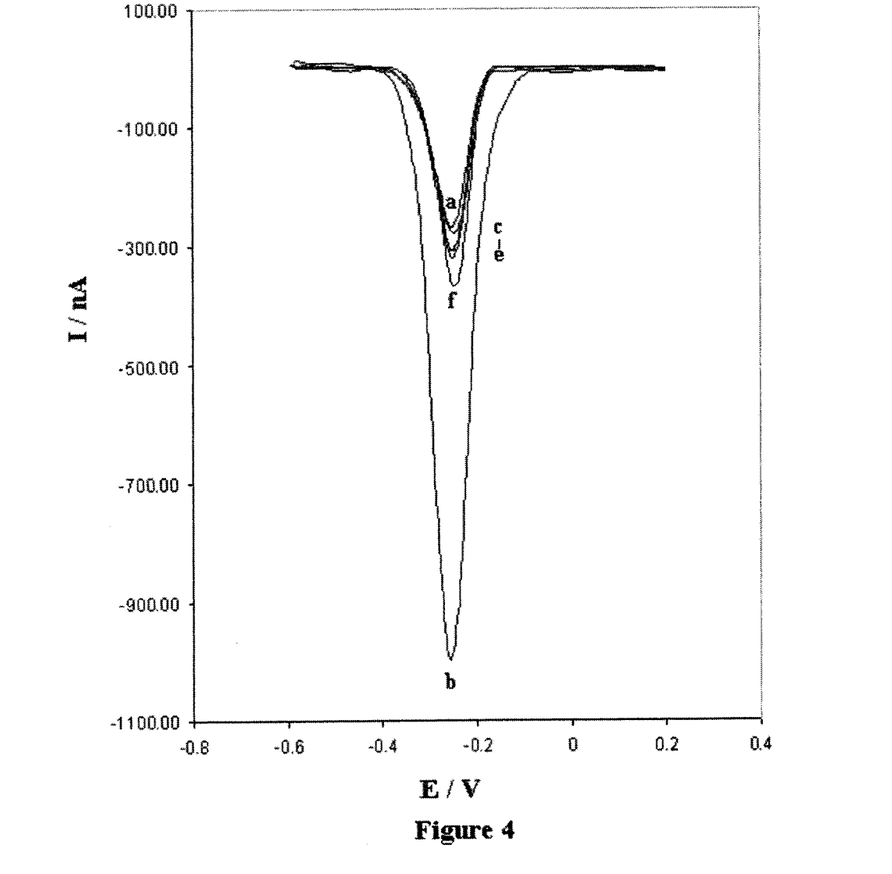
FIG. 4 shows differential pulse voltammograms for the oxidation signal of MB following self-assembly of the 13-mer PNA probe on the AuE (curve a), after hybridization with the complementary UGT1A9 PCR sample (curve b), after interaction with the non-complementary IL-4, ITS, and IL-10 PCR products (curves c through e, respectively), and after interaction with the mutant UGT1A9.SBM PCR product (curve f). All PCR products were used without denaturation of the dsDNA into ssDNAs.

FIG. 4 shows typical ADP voltammograms for the PNA probe-modified AuE before (curve a) and after (curve b) the hybridization with the complementary PCR sample. As illustrated, following the hybridization of the complementary PCR sample with the probe, the MB signal increased remarkably from 258.2±14.9 nA to 988.4±73.5 nA (shown as an oxidation current of −0.2582±0.0149 I/μA to −0.9984±0.0735 I/μA). The observed raise in the MB signal is referred to the formation of the PNA-dsDNA structure and consequently is used for the detection of a target dsDNA sequence on PCR product.

Selectivity Study for Double-Stranded PCR Product

Hybridization experiments with the non-complementary PCR products were carried out to assess whether the suggested DNA detection strategy responds selectively to the target DNA sequence. For this purpose, three different non-complementary PCR products, including human interleukin-4 and interleukin-10 promoter regions and *Thymus pubescens* internal transcribed spacer (ITS) region (SEQ ID NO: 13), were used. The DNA fragments were amplified using PCR technique and the presence of DNA bands with lengths 657, 1047, and 1138 bps, respectively, in agarose gel electrophoresis indicated the to amplification of the non-complementary PCR samples indicated (IL-4, IL-10, and ITS spacer region).

Curves c through e in FIG. 4 display the differential pulse voltammograms of the MB oxidation signal after interaction of the probe-modified electrode with the non-complementary PCR products. Upon the hybridization of ITS dsDNA, a subsequent decrease was observed in the MB current compared to that of the complementary UGT1A9 double-stranded PCR product from 988.4±73.5 nA to 308.5±27.6 nA (shown as an oxidation current of −0.9884±0.0735 I/μA to −0.3085±0.0276 I/μA). Similar results were obtained for the non-complementary IL-4 and IL-10 samples whose MB signals were a reduction current of 283.2 ±25.7 (shown as an oxidation current of −0.2832±0.0257 I/μA) and 314.6±43.1 nA (shown as an oxidation current of −0.3146±0.0431 I/μA), respectively.

Detection of Single Base Mutation on Double-Stranded PCR Product

The 166-bp UGT1A9.SBM DNA fragment containing a single base mutation was amplified using PCR (FIG. 3A) and hybridized with the PNA probe following gel extraction. The interaction between UGT1A9.SBM PCR product and the probe led to an MB signal current of 371.2±30.8 nA (shown as an oxidation current of −0.3712±0.0308I/μA) (FIG. 4, curve f), representing a significant difference between this current and that of the complementary UGT1A9 (988.4±73.5 nA) (shown as an oxidation current of −0.9884±0.0735 I/μA). This observation clearly confirmed the ability of the developed strategy to detect and discriminate the DNA mutation directly on double-stranded PCR product.

Because the above-mentioned techniques show that the interaction of a PNA probe with a double-stranded DNA (ds-oligonucleotide or PCR product) sample can be useful for detecting a target sequence or SNP without requiring dsDNA denaturation into ssDNA.

NON-PATENT REFERENCES

Check, W., "Company Probes Possibilities for PNA," CAP Today, available at http://www.cap.org/apps/portlets/contentViewerIshow.do?printFriendly=true&contentReference=cap_today/feature_stories/side1_0601.html (June 2001).

Degefa, T. H., and J. Kwak, "Electrochemical Impedance Sensing of DNA at PNA Self Assembled Monolayer," *J. Electroanalytical Chem.*, vol. 612, pp. 37-41 (2008).

Ortiz, E., et al., "PNA Molecular Beacons for Rapid Detection of PCR Amplicons," *Molecular and Cellular Probes*, vol. 12, pp. 219-226 (1998).

Karp, G., *Cell and Molecular Biology: Concepts and Experiments*, Fifth Ed., John Wiley & Sons, Inc. (2008).

Technology Feature, "Genomics: SNPs and Human Disease," *Nature* 435: 993, published online (Jun. 16, 2005).

Human Genome Project, "SNP Fact Sheet," available at http://www.ornl.gov/sci/techresources/Human_Genomegag/snps.shtml (last accessed Dec. 30, 2009).

National Center for Biotechnology Information, "SNPs: Variations on a Theme," available at http://www.ncbi.nlm.nih.gov/About/primer/snps.html (last accessed Jan. 7, 2010).

Frank-Kamenetskii, M. D., et al., "Triplex DNA Structures," *Annu. Rev. Biochem.*, vol. 64, pp. 64-95 (1995).

Rapley, R., and S. Harbron, *Molecular Analysis and Genome Discovery*, John Wiley & Sons, Ltd. (2004).

PATENT REFERENCES

| | | | |
|---|---|---|---|
| 5,656,461 | June 1995 | Demers | 435/91.1 |
| 5,700,922 | November 1993 | Cook | 536/23.1 |
| 5,985,563 | June 1997 | Hyldig-Nielsen et al. | 435/6 |
| 6,280,946 | August 1999 | Hyldig-Nielsen et al. | 435/6 |
| 6,713,255 | June 2000 | Yoshihiko et al. | 435/6 |
| WO/2009/093821 | | Lee et al. | C07H 7/00 (2006 January) |

We claim the following:

1. A method for detection of target DNA sequences using double-stranded oligonucleotides, comprising:
   creating a PNA probe that comprises a PNA sequence that is complementary to at least a portion of a target DNA sequence;
   attaching the PNA probe to an electrode, the PNA probe forming a self-assembled monolayer on the electrode;
   exposing the PNA probe to an electroactive label;
   subjecting the PNA probe to an electrochemical method to measure a baseline electrochemical signal;
   hybridizing the PNA probe with a sample of double-stranded DNA by exposing the PNA probe to the sample of double-stranded DNA to form at least one complete PNA-double-stranded DNA triplex hybrid;
   exposing the hybridized PNA probe to the electroactive label so that the electroactive label is intercalated within the at least one complete PNA-double-stranded DNA triplex hybrid;
   subjecting the hybridized PNA probe to the electrochemical method to measure a complete hybridization electrochemical signal indicative of the degree of hybridization between the PNA probe and the sample of double-stranded DNA;
   comparing the complete hybridization electrochemical signal of the hybridized PNA probe to the baseline electrochemical signal of the PNA probe; and
   determining that the target DNA sequence is present in the sample of double-stranded DNA when the complete hybridization electrochemical signal of the hybridized PNA probe is significantly greater than the baseline electrochemical signal of the PNA probe.

2. The method of claim 1, wherein the PNA probe consists of the PNA sequence and a functional group, and wherein the functional group chemically links the PNA sequence to the electrode.

3. The method of claim 2, wherein the functional group is a thiol group.

4. The method of claim 1 wherein the electrode is a gold electrode.

5. The method of claim 1, wherein the at least one complete PNA-double-stranded DNA triplex hybrid is formed when at least one strand of double-stranded DNA in the sample of double-stranded DNA is entirely complementary to the PNA probe.

6. The method of claim 1 wherein the electroactive label is methylene blue.

7. The method of claim 1, further comprising:
   hybridizing the PNA probe with a second sample of double-stranded DNA by exposing the PNA probe to the second sample of double-stranded DNA to form at least one partial PNA-double-stranded DNA triplex hybrid when one base of at least one strand of double-stranded DNA in the second sample of double-stranded DNA is not complementary to the PNA probe;
   exposing the hybridized PNA probe to the electroactive label;
   subjecting the hybridized PNA probe to the electrochemical method to measure a partial hybridization electrochemical signal indicative of the degree of hybridization between the PNA probe and the second sample of double-stranded DNA;
   comparing the partial hybridization electrochemical signal of the hybridized PNA probe to the baseline electrochemical signal of the PNA probe;
   comparing the partial hybridization electrochemical signal of the hybridized PNA probe to the complete hybridization electrochemical signal of the PNA probe; and
   determining that a single nucleotide polymorphism sequence is present in the second sample of double-stranded DNA based on the comparison of the partial hybridization electrochemical signal of the hybridized PNA probe to the baseline electrochemical signal of the PNA probe and the complete hybridization electrochemical signal of the PNA probe.

8. The method of claim 1, wherein the electrochemical method is differential pulse voltammetry.

9. The method of claim 1, wherein the baseline electrochemical signal and the complete hybridization electrochemical signal are electric current magnitudes.

10. The method of claim 7, wherein the partial hybridization electrochemical signal is an electric current magnitude.

11. The method of claim 1, wherein the PNA probe is not coupled with the electroactive label.

* * * * *

SEQUENCE LISTING

<160> NUMBER OF SEQ ID NOS: 21

<210> SEQ ID NO 1
<211> LENGTH: 13
<212> TYPE: DNA
<213> ORGANISM: Artificial Sequence
<220> FEATURE:
<223> OTHER INFORMATION: PNA oligonucleotide P275

<400> SEQUENCE: 1
agtttagtag cag

```
<210> SEQ ID NO 2
<211> LENGTH: 13
<212> TYPE: DNA
<213> ORGANISM: Artificial Sequence
<220> FEATURE:
<223> OTHER INFORMATION: DNA oligonucleotide DC275

<400> SEQUENCE: 2
ctgctactaa act                                                         13

<210> SEQ ID NO 3
<211> LENGTH: 13
<212> TYPE: DNA
<213> ORGANISM: Artificial Sequence
<220> FEATURE:
<223> OTHER INFORMATION: DNA oligonucleotide D275

<400> SEQUENCE: 3
agtttagtag cag                                                         13

<210> SEQ ID NO 4
<211> LENGTH: 20
<212> TYPE: DNA
<213> ORGANISM: Artificial Sequence
<220> FEATURE:
<223> OTHER INFORMATION: DNA oligonucleotide hIL-2

<400> SEQUENCE: 4
ggaggaagtc gtaaatttag                                                  20

<210> SEQ ID NO 5
<211> LENGTH: 20
<212> TYPE: DNA
<213> ORGANISM: Artificial Sequence
<220> FEATURE:
<223> OTHER INFORMATION: DNA oligonucleotide chIL-2

<400> SEQUENCE: 5
ctaaatttac gacttcctcc                                                  20

<210> SEQ ID NO 6
<211> LENGTH: 13
<212> TYPE: DNA
<213> ORGANISM: Artificial Sequence
<220> FEATURE:
<223> OTHER INFORMATION: DNA oligonucleotide DMM275

<400> SEQUENCE: 6
agtttagaag cag                                                         13

<210> SEQ ID NO 7
<211> LENGTH: 13
<212> TYPE: DNA
<213> ORGANISM: Artificial Sequence
<220> FEATURE:
<223> OTHER INFORMATION: DNA oligonucleotide DCMM275

<400> SEQUENCE: 7
ctgcttctaa act                                                         13

<210> SEQ ID NO 8
<211> LENGTH: 167
<212> TYPE: DNA
<213> ORGANISM: Homo sapiens

<400> SEQUENCE: 8
```
ctctggacag agagtatttg gttgcctaaa ggtaaaatct aaattttgct ctgggacaaa      60
ttccaaaaaa aattagcttt aatcaaattt acttttactt tatctttctg aaccttcaag     120
gtccaaaagc attggttaat aattctgcta ctaaacttaa cattgca                   167

<210> SEQ ID NO 9
<211> LENGTH: 21
<212> TYPE: DNA
<213> ORGANISM: Artificial Sequence
<220> FEATURE:
<223> OTHER INFORMATION: DNA oligonucleotide UGTF

<400> SEQUENCE: 9
ctctggacag agagtatttg g                                                21

<210> SEQ ID NO 10
<211> LENGTH: 23
<212> TYPE: DNA
<213> ORGANISM: Artificial Sequence
<220> FEATURE:
<223> OTHER INFORMATION: DNA oligonucleotide UGTRt

<400> SEQUENCE: 10
tgcaatgtta agtttagtag cag                                              23

<210> SEQ ID NO 11
<211> LENGTH: 167
<212> TYPE: DNA
<213> ORGANISM: Homo sapiens

<400> SEQUENCE: 11
ctctggacag agagtatttg gttgcctaaa ggtaaaatct aaattttgct ctgggacaaa      60
ttccaaaaaa aattagcttt aatcaaattt acttttactt tatctttctg aaccttcaag     120
gtccaaaagc attggttaat aattctgctt ctaaacttaa cattgca                   167

<210> SEQ ID NO 12
<211> LENGTH: 23
<212> TYPE: DNA
<213> ORGANISM: Artificial Sequence
<220> FEATURE:
<223> OTHER INFORMATION: DNA oligonucleotide UGTRa

<400> SEQUENCE: 12
tgcaatgtta agtttagaag cag                                              23

<210> SEQ ID NO 13
<211> LENGTH: 618
<212> TYPE: DNA
<213> ORGANISM: Thymus pubescens

<400> SEQUENCE: 13
aacagaccgc gaacacgtgt ttaacaaagt tggggacggt gcgggggta accctctgcc       60 gtgtcccatc tcctgccggc gtgtatcttc gggtcatgtc gtgcgggcta acgaaccccg    120
gcgcggaatg cgccaaggaa acaaaacga agcgtttccc cctggcatcc cgttcgcgga    180
gtgtgctggg ggagcagacg tctatcaaat gtcaaaacga ctctcggcaa cggatatctc   240
ggctctcgca tcgatgaaga acgtagcgaa atgcgatact tggtgtgaat tgcagaatcc   300
cgtgaaccat cgagtctttg aacgcaagtt gcgcccgaag ccattaggcc gagggcacgt   360
ctgcctgggc gtcacgcatc gcgtcgcccc ccttccccgc gctgaatgcc gggcggtcgg   420
gggcggacat tggcctcccg tgcacctccg tgcgcggctg gcccaaatgc gatccccggg   480

```
cgactggcgt cacgacaagt ggtggttgaa catctcaatc tctctcgtcg tcgtgccgtc    540
ctgtcgtcat tacgggaata gtcataaacg acccaacggt gccggtgctt aactgcacct    600
caccttcgac cgcgaccc                                                  618

<210> SEQ ID NO 14
<211> LENGTH: 19
<212> TYPE: DNA
<213> ORGANISM: Artificial Sequence
<220> FEATURE:
<223> OTHER INFORMATION: DNA oligonucleotide ITS1

<400> SEQUENCE: 14
tccgtaggtg aacctgcgg                                                  19

<210> SEQ ID NO 15
<211> LENGTH: 20
<212> TYPE: DNA
<213> ORGANISM: Artificial Sequence
<220> FEATURE:
<223> OTHER INFORMATION: DNA oligonucleotide ITS4

<400> SEQUENCE: 15
tcctccgctt attgatatgc                                                 20

<210> SEQ ID NO 16
<211> LENGTH: 1047
<212> TYPE: DNA
<213> ORGANISM: Homo sapiens

<400> SEQUENCE: 16
agctttggga gactgaggta ggaggatcac ttgagcccag gaatttgaga tgagcctagg     60
caacatagtg agactcttat ctctatcaaa aaataaaaat aaaaatgagc caggcatggt    120
gcggtggacc acgcacctac tgctaggggg gctgaggtgg gaggatcatt gagcctggga    180
ggttgaggct gcagtgatcc ctgatcaaac attgcatttc agcctgggtg acagagtgag    240
accctgtctc agaaaaaaaa aaaaaaagtc attcctgaaa cctcagaata gacctacctt    300
gccaagggct tccttatggg taaggacctt atggacctgc tgggacccaa actaggcctc    360
acctgatacg acctgtcctt ctcaaaacac taaacttggg agaacattgt cccccagtgc    420
tggggtagga gagtctgcct gttattctgc ctctatgcag agaaggagcc ccagatcatc    480
ttttccatga caggacagtt tccaagatgc cacctgtact tggaagaagc caggttaaaa    540
tacttttcaa gtaaaacttt cttgatatta ctctatcttt ccccaggagg actgcattac    600
aacaaattcg gacacctgtg gcctctccct tctatgcaaa gcaaaaagcc agcagcagcc    660
ccaagctgat aagattaatc taaagagcaa attatggtgt aatttcctat gctgaaactt    720
tgtagttaat ttttttaaaaa ggtttcattt tcctattggt ctgatttcac aggaacattt    780
tacctgtttg tgaggcattt tttctcctgg aagagaggtg ctgattggcc ccaagtgact    840
gacaatctgg tgtaacgaaa atttccaatg taaactcatt ttccctcggt ttcagcaatt    900
ttaaatctat atatagagat atctttgtca gcattgcatc gttagcttct cctgataaac    960
taattgcctc acattgtcac tgcaaatcga cacctattaa tgggtctcac ctcccaactg   1020
cttccccctc tgttcttcct gctagca                                      1047

<210> SEQ ID NO 17
<211> LENGTH: 21
<212> TYPE: DNA
```

```
<213> ORGANISM: Artificial Sequence
<220> FEATURE:
<223> OTHER INFORMATION: DNA oligonucleotide IL4-F

<400> SEQUENCE: 17
agctttggga gactgcaggt a                                              21

<210> SEQ ID NO 18
<211> LENGTH: 20
<212> TYPE: DNA
<213> ORGANISM: Artificial Sequence
<220> FEATURE:
<223> OTHER INFORMATION: DNA oligonucleotide IL4-R

<400> SEQUENCE: 18
tgctagcagg aagaacagag                                                20

<210> SEQ ID NO 19
<211> LENGTH: 1239
<212> TYPE: DNA
<213> ORGANISM: Homo sapiens

<400> SEQUENCE: 19
ccaagacaac actactaagg cttctttggg aaggggaagt agggataggt aagaggaaag      60
taagggacct cctatccagc ctccatggaa tcctgacttc ttttccttgt tatttcaact    120
tcttccaccc catcttttaa actttagact ccagccacag aagcttacaa ctaaaagaaa    180
ctctaaggcc aatttaatcc aaggtttcat tctatgtgct ggagatggtg tacagtaggg    240
tgaggaaacc aaattctcag ttggcactgg tgtacccttg tacaggtgat gtaacatctc    300
tgtgcctcag tttgctcact ataaaataga gacggtaggg gtcatggtga gcactacctg    360
actagcatat aagaagcttt cagcaagtgc agactactct tacccacttc ccccaagcac    420
agttggggtg ggggacagct gaagaggtgg aaacatgtgc ctgagaatcc taatgaaatc    480
ggggtaaagg agcctggaac acatcctgtg accccgcctg tcctgtagga agccagtctc    540
tggaaagtaa aatggaaggg ctgcttggga actttgagga tatttagccc accccctcat    600
ttttacttgg ggaaactaag gcccagagac ctaaggtgac tgcctaagtt agcaaggaga    660
agtcttgggt attcatccca ggttgggggg acccaattat ttctcaatcc cattgtattc    720
tggaatgggc aatttgtcca cgtcactgtg acctaggaac acgcgaatga gaacccacag    780
ctgagggcct ctgcgcacag aacagctgtt ctccccagga aatcaacttt ttttaattga    840
gaagctaaaa aattattcta agagaggtag cccatcctaa aaatagctgt aatgcagaag    900
ttcatgttca accaatcatt tttgcttacg atgcaaaaat tgaaactaa gtttattaga     960 gaggttagag aaggaggagc tctaaggaga aaaaatcctg tgccgggaaa ccttgattgt    1020
ggctttttaa tgaatgaaga ggcctccctg agcttacaat ataaagggg gacagagagg    1080 tgaaggtcta cacatcaggg gcttgctctt gcaaaaccaa accacaagac agacttgcaa    1140
aagaaggcat gcacagctca gcactgctct gttgcctggt cctcctgact ggggtgaggg    1200
ccagcccagg ccagggcacc cagtctgaga acagctgca                          1239

<210> SEQ ID NO 20
<211> LENGTH: 20
<212> TYPE: DNA
<213> ORGANISM: Artificial Sequence
<220> FEATURE:
<223> OTHER INFORMATION: DNA oligonucleotide IL10-F

<400> SEQUENCE: 20
```

```
ccaagacaac actactaagg                                              20

<210> SEQ ID NO 21
<211> LENGTH: 19
<212> TYPE: DNA
<213> ORGANISM: Artificial Sequence
<220> FEATURE:
<223> OTHER INFORMATION: DNA oligonucleotide IL10-R

<400> SEQUENCE: 21
tgcagctgtt ctcagactg                                               19
```